United States Patent
Colin

(10) Patent No.: US 7,741,129 B2
(45) Date of Patent: Jun. 22, 2010

(54) METHOD FOR TREATING MAGNETIC PARTICLES AND BIOLOGICAL ANALYSIS DEVICE USING MAGNETS

(75) Inventor: Bruno Colin, Marcy l'Etoile (FR)

(73) Assignee: BioMerieux S.A., Marcy l'Etoile (FR)

( * ) Notice: Subject to any disclaimer, the term of this patent is extended or adjusted under 35 U.S.C. 154(b) by 0 days.

(21) Appl. No.: 12/102,830

(22) Filed: Apr. 14, 2008

(65) Prior Publication Data

US 2008/0257825 A1      Oct. 23, 2008

Related U.S. Application Data

(62) Division of application No. 10/483,121, filed as application No. PCT/FR02/02409 on Jul. 9, 2002, now Pat. No. 7,396,690.

(30) Foreign Application Priority Data

Jul. 9, 2001     (FR)     .................................. 01 09067

(51) Int. Cl.
G01N 33/553     (2006.01)

(52) U.S. Cl. ...................................................... 436/526
(58) Field of Classification Search ....................... None
See application file for complete search history.

(56) References Cited

U.S. PATENT DOCUMENTS 5,998,224 A  *  12/1999  Rohr et al. ................... 436/526

* cited by examiner

*Primary Examiner*—Ann Y Lam
(74) *Attorney, Agent, or Firm*—Foley & Lardner LLP

(57) ABSTRACT

A method for treating magnetic particles present in a solution in a container by redispersion, rinsing or displacement, the particles having novel characteristics under the effect of a specific magnet and being associated or not with biological entities. The magnetic particles undergo at least one low-intensity magnetization where they are disposed in filaments oriented according to the north-south axis of the magnet; the magnetization source and/or container is/are displaced while the magnetic effect is maintained on the magnetic particles; the magnetization source and/or container is/are displaced or the magnetization is stopped, in order to suppress the magnetic field on the magnetic particles. Preferably, the invention can be used in the field of biology.

10 Claims, 2 Drawing Sheets

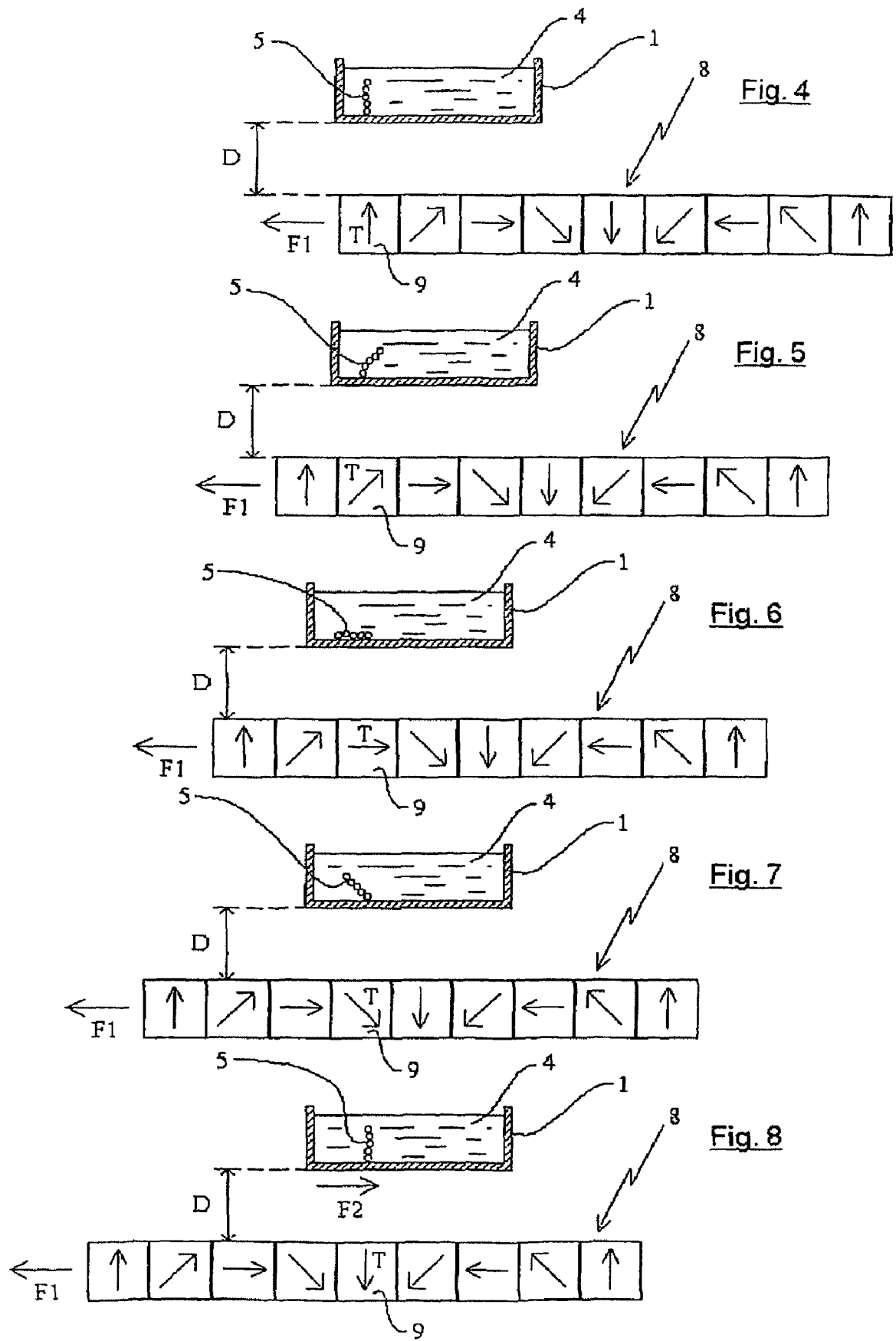

METHOD FOR TREATING MAGNETIC PARTICLES AND BIOLOGICAL ANALYSIS DEVICE USING MAGNETS

PRIOR RELATED APPLICATIONS

This is a divisional application of U.S. Ser. No. 10/483,121 filed May 14, 2004 now U.S. Pat. No. 7,396,690, which is a U.S. national stage application of International Application PCT/FR02/02409 filed Jul. 9, 2002 which, in turn, claims priority to French Application 0109067 Filed Jul. 9, 2001, and all prior related applications cited herein are incorporated by reference in their entireties.

DESCRIPTION

The present invention relates to a method for treating magnetic particles present in solution in a vessel, the magnetic particles being associated or not to biological entities (antibodies, antigens, nucleic acids, etc.). The envisaged treatment can consist of resuspension, washing or movement of the magnetic particles which have novel characteristics under the action of a specific magnet. The present invention also relates to magnet configurations, at least one of which allows the above-mentioned method to be carried out.

The method according to the invention can be useful in the field of biological diagnosis, for example, to detect an illness from the analysis of biological molecules (protein, nucleic acid, etc.) extracted from biological samples (urine, blood, cerebrospinal fluid, sediment, sputum). In this context of research, the intention is notably to be able to extract and concentrate these biological molecules, in conditions compatible with activity tests for some proteins or nucleic acids, so as to reveal the presence of a particular biological molecule in sick persons. One method consists in associating these biological molecules to magnetic particles. These molecules are called recognition molecules. In a particular embodiment, these can be used to associate or hybridise to specific target molecules in these recognition molecules. Furthermore, it is also possible to precisely detect these associations or hybridisations, between recognition molecules and target molecules, via detection molecules.

Subjected to various magnetic fields, these magnetic particles, which form a solid support, allow the trapping of the biological molecules which are associated thereto so as to concentrate them in a solution, or to extract them from a solution. Thus, a method allowing the concentration or the deletion of magnetic particles associated to biological molecules has been described in application WO-A-99/59694. Magnets that are sufficiently powerful to trap the magnetic particles are disposed along a tube inside which the panicles in solution circulate, so as to obtain a solution, free of magnetic particles and therefore free of the biological molecules which were associated thereto.

This technique for trapping magnetic particles associated to biological molecules is also used for washing steps of these biological molecules through a series of steps of washing liquid suction and resuspension in a new washing liquid. Thus, in automated machines of the type allowing immunoassays to be carried out, the magnetic particles, in solution in the automated machine's tanks, are trapped by a laterally applied magnetic field, and end up in clusters on the tank walls. The liquid is sucked out whereas the magnetic particles are retained. This suction step is followed by a resuspension step. For this step, the magnetic particles are subjected to a reverse magnetic field, and to sudden injection of washing liquid. A series of suction and resuspension steps thus allows washing of the particles.

Another washing technique has been described in application WO-A-01/05510. The magnetic particles are present in solution in a tank or a tube. Washing is effected by passing the magnetic particles from one side of the tank or tube to the other by means of a series of magnets, applied on one side of the tank, then on the other. The trapping of these particles at the bottom of the tube by a magnet allows, in a manner comparable to that described above, the suction of the liquid in which the magnetic particles were diluted. Patent application WO-A-01/05510 proposes such a washing technique, from which our invention differs with its own additional technical characteristics, namely:

subjecting magnetic particles in solution in a vessel to at least low-intensity magnetisation, and positioning the magnetic particles in the form of filaments oriented along the north-south axis of the magnetisation source.

These two points are therefore not found in this document, which in no way specifies the magnetisation intensity, and which keeps the magnetic particles in pellet form. Furthermore, the article by Fermigier M et al. relates to a washing technique which proposes additional information on linear aggregates under an alternating field.

If it can be considered that the magnetic particles are in the form of filaments, this is not due to at least low-intensity magnetisation.

The association of magnetic particles to biological particles also allows the movement of these biological molecules from one compartment to another to allow their concentration, for example. This is the case in patent application FR00/15417 of 17 Nov. 2000. Thus, in biochips, a plane and constant magnetic field allows the draining of these particles from one point to another during the steps for concentrating these particles in a given compartment of the biochip.

However, a low-intensity magnetic field, though allowing rapid and effective trapping, can cause the formation of particle clusters, which are often difficult to resuspend if an additional agitation step is not carried out. The reduction of the effectiveness of the washing of these magnetic particles is also the result of the formation of these clusters, since the washing liquid cannot reach all of the particles. Finally, this constant and high-intensity magnetic field generally does not allow the draining of all of the particles from one given point to another, due to the large frictional forces which are linked to this movement. This can be detrimental to the results of the tests which will be subsequently carried out (false negatives, false positives, reduction in sensitivity and specificity) or when it is desired to recover all of the biological molecules associated to the magnetic molecules, for economic reasons or reasons of biological material availability.

The present invention proposes to resolve all of the disadvantages of the prior art by presenting a particular arrangement of the magnetic particles in a liquid which promotes the resuspension, washing and/or movement thereof. The invention is based on the arrangement in filaments of the magnetic particles in a liquid, in response to a particular magnetic field, generally of low-intensity, which filaments are arranged along the south-north axis of the magnet inducing the magnetic field.

To this aim, the present invention relates to a method for treating magnetic particles present in solution in a vessel, the magnetic particles being associated or not to biological entities (antibodies, antigens, nucleic acids, etc.), the method consisting in:

subjecting said magnetic particles (5) to a constant magnetic field in the form of magnetisation which is a function essentially of two values, T and D, where:

T corresponds to the magnetic induction of the magnetisation source (7 or 9), expressed for example in milliTesla (mT), and D corresponds to the distance separating this magnetisation source (7 or 9) from the bottom (3) of the vessel (1), expressed for example in millimeters (mm), such that when T is between 5 and 400 mT, D is less than or equal to 50 mm for ESTAPOR (registered trade mark—reference: M1 70/60) magnetic particles (5), with a diameter substantially less than 1µ (Merk eurolab—Pitiviers France), such that said magnetic particles are disposed in filaments oriented along the north-south axis of the magnetisation source, moving the magnetisation source and/or the vessel, while maintaining magnetisation on the magnetic particles, and suppressing magnetisation on the magnetic particles by moving said magnetisation source and/or the vessel and/or stopping the magnetisation source.

Preferably, magnetic induction T of the magnetisation source is between 10 and 50 mT, and the distance separating this magnetisation source from the vessel is between 3 and 15 mm, for ESTAPOR (registered trade mark) magnetic particles defined above.

When the distance separating the magnetisation source from the bottom of the vessel is zero, i.e. said source and said bottom are contacting each other, magnetic induction T of the magnetisation source is less than 5 mT for ESTAPOR (registered trade mark) magnetic particles defined above.

In the case where the method allows washing of the magnetic particles, the movement of the magnetisation source and/or the vessel, while maintaining the magnetic effect on the magnetic particles, is achieved by the variation between −90° and +90° of the angle between the north-south axis of said magnetisation source and the axis of said vessel. This arrangement thus allows more effective washing of the particles: the low-intensity magnetic field, subjected to a rotation of an angle of −90° to +90°, induces the motion of the filaments which are inclined from one side to the other. In comparison to the prior art, this arrangement increases the contact between the magnetic particles and the washing liquid and thereby increases the washing effectiveness without requiring resuspension of the particles.

In the case where the method allows the resuspension of the magnetic particles, the magnetisation of the magnetisation source is maintained on the magnetic particles during the injection of a liquid for recovering said magnetic particles within the vessel, then is cut off after this injection. This device thus allows more easy resuspension of the magnetic particles. When the liquid volume increases, the magnetic field becomes too weak to maintain the particles in filaments, which therefore resuspend spontaneously. Compared to the prior art, the addition of liquid is sufficient according to the invention to resuspend all of the particles without an additional agitation step or reverse magnetic field.

In a preferred embodiment of the method allowing the resuspension of the magnetic particles, said magnetic particles, are disposed in filaments oriented along the north-south axis of the magnetisation source and parallel to the injection motion of the recovery liquid.

In the case where the method allows for the movement of magnetic particles, the movement of the magnetisation source and/or the vessel, while maintaining magnetisation on the magnetic particles, is achieved by the 360° rotation of the angle between the north-south axis of said magnetisation source and the axis of said vessel. When this magnetic field is subjected to successive 360° rotations and to low-speed movement along a horizontal axis, the particles, forming a filament, tilt until lying fully, then lift from the opposite side, then tilt, lie, lift, etc., and thus move progressively forward in the opposite direction to the lateral movement of the magnetic field. in comparison to the prior art, the frictional forces associated with the movement of these particles are weaker, which allows the number of particles directed from one point to another to be increased.

In the latter case, the 360° rotation is effected a plurality of times so as to obtain appropriate movement of the magnetic particles.

The present invention also relates to a biological analysis apparatus, for example for immunoassays, which apparatus includes guiding and movement means for reaction vessels over at least one path including a predetermined number of positions. This apparatus comprises a magnet configuration for each path, the magnet configuration being made up:

upstream, of a plurality of high-intensity magnetisation sources, such that the magnetic particles are agglomerated against the wall of the vessel, and downstream, of a low-intensity magnetisation source, as defined above, such that said magnetic particles are disposed in filaments oriented along the north-south axis of the magnetisation source.

According to an alternative, each high-intensity magnetisation source is of a magnetisation induction which is 20 to 100 times, preferably 30 to 60 times greater than the low-intensity magnetisation source, and each high-intensity magnetisation source is at a distance from the vessel which is 5 to 20 times, preferably 10 to 15 times less than the distance from the low-intensity magnetisation source.

According to another alternative, each high-intensity magnetisation source is in a position perpendicular to the low-intensity magnetisation source, in relation to the vessel.

According to yet another alternative, each high-intensity magnetisation source is in a lateral position to the axis passing through the opening and the bottom of the vessel, and the low-intensity magnetisation source is located beneath said bottom of said vessel, opposite the opening thereof.

Still according to an alternative, the closer the position of the high-intensity magnetisation source, along the path including a predetermined number of positions, to the low-intensity magnetisation source, the closer the position of said high-intensity magnetisation source to the bottom of the vessel.

According to another alternative, the high-intensity magnetisation source is made up of:

a row of magnets located on the same side of the vessels, or two rows of magnets located on either side of the vessels, the magnets of a same row being positioned side-by-side, with the north-south poles identically oriented.

According to the latter alternative, the high-intensity magnetisation source comprises at least one reversed polarisation magnet (reverse field) which promotes the "release" of the magnetic particles.

The accompanying drawings are given by way of explanatory example and are in no way limiting. They will allow the invention to be more easily understood.

FIG. 4 shows a sectional view of a flat-bottomed vessel, where a single filament of magnetic particles is illustrated to facilitate understanding of the magnetic particle movement method. The single magnet of the compound magnet which acts on the magnetic particles is not inclined.

FIG. 5 shows an identical view to the preceding one, but the single magnet which acts on the magnetic particles is inclined by 45° to that of FIG. 4.

FIG. 6 shows an identical view to the preceding one, but the single magnet which acts on the magnetic particles is inclined by 90° to that of FIG. 4.

FIG. 7 shows an identical view to the preceding one, but the single magnet which acts on the magnetic particles is inclined by 135° to that of FIG. 4.

Finally, FIG. 8 shows an identical view to the preceding one, but the single magnet which acts on the magnetic particles is inclined by 180° to that of FIG. 4.

Figure 1:
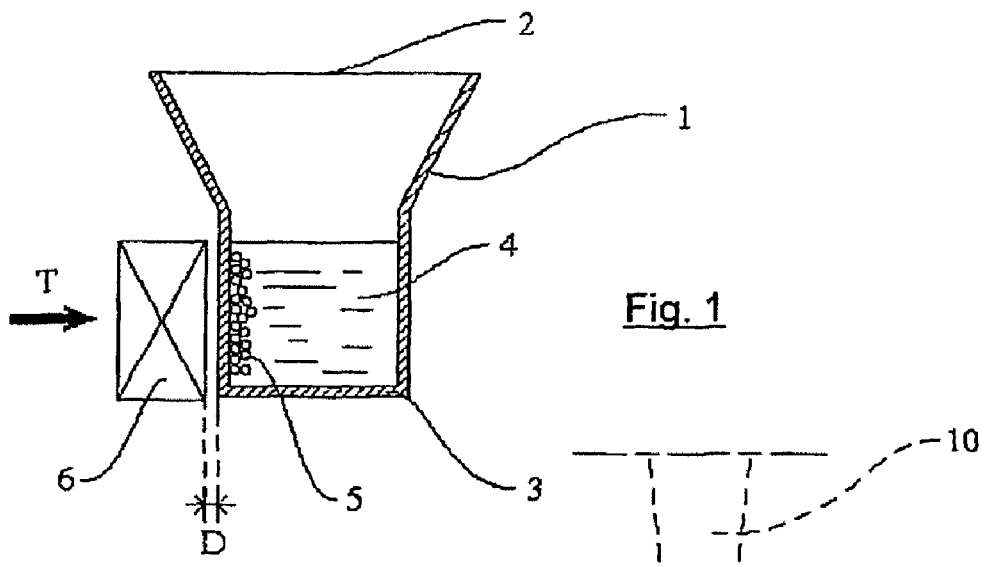
FIG. 1 shows a vessel containing magnetic particles which are agglomerated under the action of a high-intensity magnet, according to the prior art.

The embodiment shown in FIG. 1 represents the prior art most commonly used for many years to trap magnetic particles 5 in tanks used in biological analysis automated machines. Magnet 6 is powerful, with a magnetic intensity T of between, for example, 450 and 500 mT and a distance separating said magnet 6 from the side of vessel 1 which is a few millimetres. Under these conditions, it is noted that magnetic particles 5 are amalgamated together to form a deposit. It is clearly apparent that in this form, the resuspension of said magnetic particles 5 is not facilitated and will require a sufficiently powerful injection of liquid, at a quite specific angle. The power of this injection must however be well controlled to avoid splashes, which can soil the inside of automated machines, and to prevent the deterioration of the biological constituents present within the tank, which would risk distorting the biological results observed. Furthermore, there is never total resuspension, since some magnetic particles 5 remain amalgamated together even once in solution.

Figure 2:
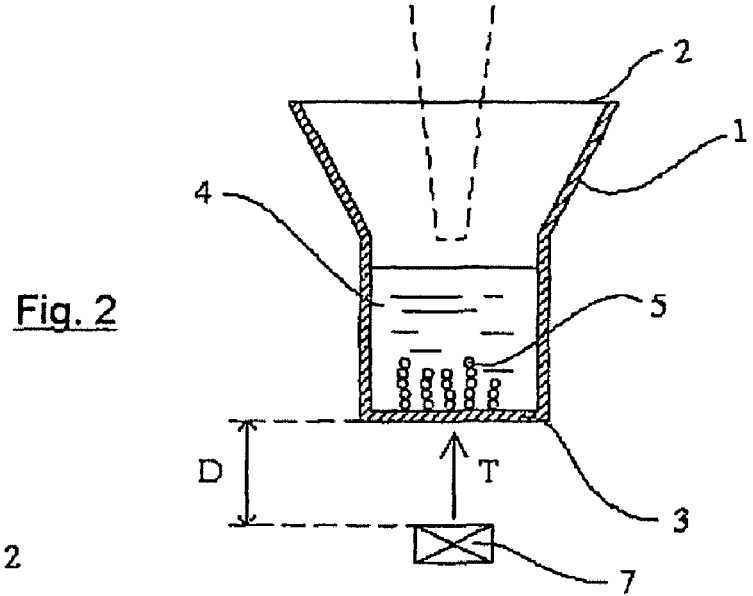
FIG. 2 shows an identical view to the preceding one, but in which the magnetic particles are arranged in filaments along the north-south axis of a low-intensity magnet.

The present invention proposes a solution which not only allows the trapping, but also the washing, the resuspension and the movement of said magnetic particles 5. Thus, it is noted in FIG. 2 that, under low magnetic intensity magnetisation T of between for example 10 and 20 mT and at a distance separating said magnet 7 from bottom 3 of vessel 1 which is 13 millimetres, magnetic particles 5 are not amalgamated but are in the form of filaments where magnetic particles 5 of a same filament are on top of each other along a substantially longitudinal axis. It is clearly apparent that in this form the resuspension of said magnetic particles 5 is much more simple. Furthermore, the injection of a liquid, for example by means of a pipette, of which only nozzle 10 is seen in FIG. 2, will facilitate this resuspension. The technique is further improved if the axis, along which the injection of liquid is effected, is directed against bottom 3 of vessel 1 and if said longitudinal axis of the filaments is substantially parallel to said injection axis.

The following examples are given by way of illustration and are in no way limiting. They will allow the invention to be more easily understood.

EXAMPLE 1

Choice of the Structural Characteristics of a Magnet According to the Invention to Allow the Resuspension of the Magnetic Particles The magnetic particles are in solution in tanks 1 for Magia (registered trade mark) automated machines. The resuspension steps comprise:

1—a suction step: ESTAPOR (registered trade mark—reference: M1 70/60) magnetic particles 5, with a diameter substantially less than 1μ (Merk eurolab—Pitiviers France) are trapped by a magnetic field with an intensity of 450 to 500 mT laterally applied via conventional magnet 6, and become clustered on the tank walls. This is for example what is shown in FIG. 1, but at bottom 3 of a vessel 1. Liquid 4, contained by this vessel 1, is sucked out whereas magnetic particles 5 are retained. The volume remaining after suction is of the order of 50 to 80 μl.

2—a resuspension step: This resuspension step is effected by the lateral application of a reverse magnetic field and the sudden addition of liquid 4 into vessel 1 of the order of 450 μl to 1 ml. This resuspension step is only partial since small clusters of particles remain on the side walls of vessels 1.

3—repetition of the preceding steps: Steps 2 and 3 are repeated as often as is required by the immunoassay apparatus to carry out the distribution, suction and concentration steps.

4—a last resuspension step: This consists in resuspending all of magnetic particles 5 before the analysis step. In order to do so, a first magnetic field with an intensity of 120 mT is located beneath vessels 1 at a distance of 3 mm. Liquid 4 is sucked out, particles 5 being retained in a comparable manner to that which is described in step 1. This first magnetic field is in no way compulsory, even though it brings about some advantages for draining the magnetic particles onto the bottom of vessel 1, or for resuspension. Said magnetic particles 5, in remaining liquid volume 4, of between 50 and 80 μl, are subjected to a second magnetic field with a varying value, located beneath the tanks at a distance which itself varies. The results obtained are described in the following table:

TABLE

| | Study of the relation between D (in mm) and T (mT) | | | | | |
|---|---|---|---|---|---|---|
| D/T | 1 mT | 5 mT | 10 mT | 20 mT | 50 mT | 400 mT |
| Contacting | In solution | Filaments | Amalgam | Amalgam | Amalgam | Amalgam |
| 1 mm | In solution | In solution | Filaments | Amalgam | Amalgam | Amalgam |
| 10 mm | In solution | In solution | In solution | Filaments | Amalgam | Amalgam |
| 50 mm | In solution | In solution | In solution | In solution | In solution | Filaments |
| 100 mm | In solution | In solution | In solution | In solution | In solution | In solution |

In the above-mentioned cases, magnetic particles 5 become arranged spontaneously, under the action of this weak magnetic field, in the form of filaments. These particle 5 filaments are then easily resuspended by adding 450 to 500 μl of liquid through opening 2 of vessel 1. It is to be understood that these evaluations of the in-solution or amalgamated filamentous nature of the magnetic particles are the result of an arbitrary scale which nevertheless is common to all of the tested biological samples and mediums. This scale is valid for this experiment as well as for all of the following experiments. It can be defined in the following manner:

"In solution", there is no particular concentration in liquid sample 4 where the magnetic particles appear to be homogeneously distributed throughout said sample 4.

"Filaments", there is a certain concentration in liquid sample 4 where the magnetic particles are structured against part of the wall of vessel 1 opposite magnet 7. Such filaments are for example clearly shown in FIG. 2. Binocular magnification shows light incident passing between the filaments.

"Amalgam", there is a particular concentration in liquid sample 4 where the magnetic particles are concentrated against part of the wall of vessel 1 opposite magnet 7. Binocular magnification shows no light incident passing through the amalgam.

EXAMPLE 2

Magnetic Particle Washing

Magnetic particles 5 are in solution in tanks 1 for Magia (registered trade mark) automated machines. As in Example 1, magnetic particles 5 are subjected to low-intensity magnetisation, comprising adequate values (D=13 mm and T=10 mT) to obtain filaments with magnetic particles 5 identical to Examples 1.

Figure 3:
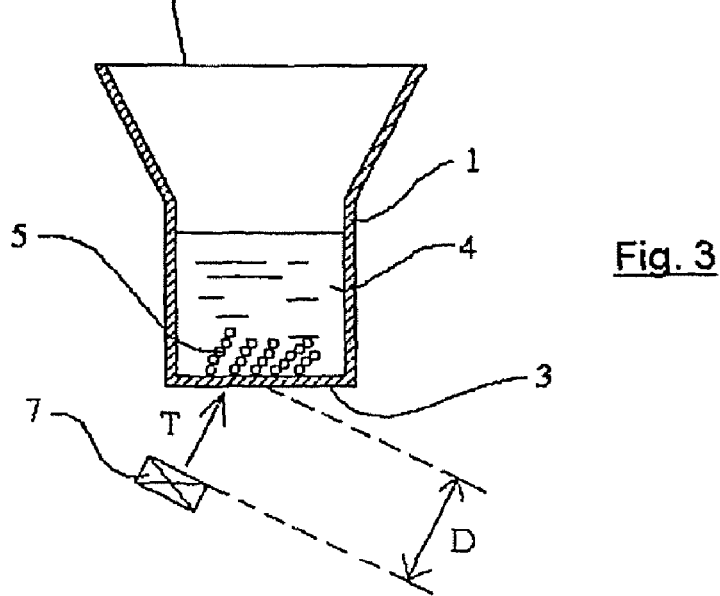
FIG. 3 shows a view identical to FIG. 2 but in which the magnetic particles arranged in filaments along the north-south axis of a low-intensity magnet are subjected to a rotation of substantially 300 in relation to the central and vertical axis of the vessel containing the magnetic particles. This configuration facilitates the washing of said magnetic particles.

The washing step consists essentially in moving magnet 7, as is clearly shown in FIG. 3 so as to allow inclination of said filaments. It is to be understood that vessel 1 can also be moved, or both simultaneously, i.e. magnet 7 and vessel 1. Increasing the number of this type of movement thus allows the washing effectiveness to be substantially improved.

This washing effectiveness is particularly increased by inducing, when the magnetic particles are arranged in filaments, a rotation oscillating between −90° and +90° to the second low-intensity magnetic field described in Example 1. FIG. 3 thus illustrates the arrangement of the magnetic particles in filaments 1 during a rotation of −30° (A) and +30° (B).

These particle filaments can then be easily resuspended by adding 450 to 500 μl of liquid, as has already been described in Example 1.

EXAMPLE 3

Magnetic Particle Movement

Here again as in Examples 1 and 2, magnetic particles 5 are subjected to low-intensity magnetisation, comprising adequate values (D=13 mm and T=10 mT) to obtain filaments with magnetic particles 5 identical to Examples 1 and 2.

FIGS. 4 to 8 depict more precisely what is meant by movement. These figures only show rotation through 180°, by increments of 45°, but it is clearly apparent that several 360° rotations allow the amplitude of this movement to be considerably enhanced. In a preferred embodiment, magnet 8 is in the form of a "band". It is a compound magnet made up of a plurality of single magnets 9, each magnet 9 having a different north-south polarisation from the adjacent magnets, with the polarisation variation being 45° in the illustrated embodiment.

It is noted that when, for example, magnet 8 is moved substantially along its longitudinal axis in the direction of F1 of FIGS. 4 to 8, magnetic particles 5 are moved at the same time in the reverse direction to F2 of FIG. 8, where the difference in position between FIG. 4 and this same filament in FIG. 8 is clearly noted.

EXAMPLE 4

Magnet Configuration

As regards the magnet configurations associating conventional magnets 6 and magnets 7 according to the invention, these can be used in biological analysis apparatuses, for example for immunoassays, apparatuses including guiding and moving means for reaction vessels 1 along at least one path including a predetermined number of positions. Such a type of apparatus is clearly described in patent applications EP-A-0.837.331 and WO-A-00/16075.

Such an apparatus comprises a magnet configuration for each path, magnet configuration 6 and 7 or 9 being made up in the following manner:

upstream, of a plurality of high-intensity magnetisation sources 6, such that magnetic particles 5 are agglomerated against the wall of the vessel, and downstream, of a low-intensity magnetisation source 7 or 9, as described in the preceding examples, such that said magnetic particles 5 are in the form of filaments oriented along the north-south axis of the magnetisation source.

The relations which exist between each high-intensity magnetisation source 6 and low intensity magnetisation source 7 or 9 are as follows:

a 20 to 100 times, preferably 30 to 60 times greater magnetic induction T, and a 5 to 20 times, preferably 10 to 15 times smaller distance D from vessel 1.

According to both patent applications cited above, each high-intensity magnetisation source 6 is laterally positioned in relation to the axis passing through opening 2 and bottom 3 of vessel 1. Furthermore, each high-intensity magnetisation source 6 is perpendicularly positioned to low-intensity magnetisation source 7 or 9, in relation to vessel 6. Preferably, low-intensity magnetisation source 7 or 9 is located beneath said bottom 3 of said vessel 1.

In the preferred configuration described above, the closer the position of high-intensity magnetisation source 6, along the path including a predetermined number of positions, to low-intensity magnetisation source 7 or 9, the closer the position of said high-intensity magnetisation source 6 to bottom 3 of vessel 1.

It is possible to have at least two different versions of the magnet 6 configuration. Firstly, high-intensity magnetisation source 6 is made up of a row of magnets located on the same side of vessels 1, magnets 6 being positioned side-by-side, with the north-south poles identically oriented. Secondly, high-intensity magnetisation source 6 is made up of two rows of magnets located on either side of vessels 1, the magnets of a same row being positioned side-by-side, with the north-south poles identically oriented, i.e. with the magnets repelling each other.

To facilitate the release of magnetic particles 5, high-intensity magnetisation source 6 comprises at least one reversed polarisation magnet (reverse field). Generally, this magnet is located in the most downstream position possible, i.e. closest to low-intensity magnet 7.

REFERENCES

1. Vessel
2. Opening of vessel 1
3. Bottom of vessel 1
4. Liquid contained in vessel 1
5. Magnetic particles contained in liquid 4
6. Magnet according to the prior art
7. Single magnet or magnetisation source according to the invention
8. Compound magnet or magnetisation source according to the invention
9. Single magnet of compound magnet 8 which acts on magnetic particles 5
10. Pipette nozzle
D. Distance separating magnetisation source 7 from the bottom of vessel 1
F1. Movement of magnet 8 along its longitudinal axis
F2. Movement of particles 5 depending on the movement of magnet 8 along F1
T. Magnetic induction of magnetisation source 7

The invention claimed is:

1. A method for treating magnetic particles present in solution in a vessel, wherein the magnetic particles are capable of being associated with biological entities, the method comprising:
    a) subjecting the magnetic particles to a constant magnetic field in the form of magnetisation that is a function of T and D, wherein:
        the magnetisation is generated by a magnetisation source;
        T is a magnetic induction of the magnetisation source, expressed in milliTesla (mT),
        D is the distance separating the magnetisation source from the bottom of the vessel, expressed in millimeters (mm),
    wherein T is between 5 and 400mT and D is less than or equal to 50mm, and
        wherein the magnetisation disposes the magnetic particles in filaments that are oriented along the north-south axis of the magnetisation source,
    b) moving the magnetisation source or the vessel or both, while maintaining magnetisation on the magnetic particles, and
    c) suppressing magnetisation on the magnetic particles by moving the magnetisation source or the vessel or both, or by stopping the magnetisation source.

2. The method of claim 1, wherein T is between 10 and 50 mT, and D is between 3 and 15 mm.

3. The method of claim 1, further comprising washing the magnetic particles, wherein the washing occurs while moving the magnetisation source or the vessel or both while also maintaining a magnetic effect on the magnetic particles and varying movement between an angle of −90° and +90° between the north-south axis of the magnetisation source and the axis of the vessel.

4. The method of claim 1, further comprising resuspending the magnetic particles, wherein the magnetisation is maintained on the magnetic particles during injection of a liquid for recovering the magnetic particles within the vessel, wherein the magnetisation is stopped after the injection.

5. The method of claim 4, wherein the magnetic particles are disposed in filaments oriented along the north-south axis of the magnetisation source and parallel to the injection motion of the recovery liquid.

6. The method of claim 1, wherein the moving the magnetisation source or the vessel or both, while maintaining magnetisation on the magnetic particles, is achieved by a 360° rotation of the angle between the north-south axis of the magnetisation source and the axis of the vessel.

7. The method of claim 6, wherein the 360° rotation occurs a plurality of times.

8. The method of claim 1, wherein the biological entities are selected from the group consisting of antibodies, antigens and nucleic acids.

9. The method of claim 1, wherein the magnetic particles have a diameter that is less than 1 µm.

10. A method for treating magnetic particles present in solution in a vessel, wherein the magnetic particles are capable of being associated with biological entities, the method comprising:
    a) subjecting the magnetic particles to a constant magnetic field in the form of magnetisation that is a function of T and D, wherein:
        the magnetisation is generated by a magnetisation source;
        T is a magnetic induction of the magnetisation source, expressed in milliTesla (mT),
        D is the distance separating the magnetisation source from the bottom of the vessel, expressed in millimeters (mm),
    wherein T is less than 5 mT, and D is zero, and
        wherein the magnetisation disposes the magnetic particles in filaments that are oriented along the north-south axis of the magnetisation source,
    b) moving the magnetisation source or the vessel or both, while maintaining magnetisation on the magnetic particles, and
    c) suppressing magnetisation on the magnetic particles by moving the magnetisation source or the vessel or both, or by stopping the magnetisation source.

* * * * *